(12) United States Patent
Pedrazzini

(10) Patent No.: US 8,800,747 B2
(45) Date of Patent: Aug. 12, 2014

(54) APPARATUS FOR LOADING BIOLOGICAL MATERIAL CONTAINERS IN A CONVEYING SYSTEM

(75) Inventor: Gianandrea Pedrazzini, Paradiso (CH)

(73) Assignee: INPECO Holding Ltd., Valletta (MT)

( * ) Notice: Subject to any disclaimer, the term of this patent is extended or adjusted under 35 U.S.C. 154(b) by 1046 days.

(21) Appl. No.: 12/864,428

(22) PCT Filed: Jan. 20, 2009

(86) PCT No.: PCT/EP2009/050597
§ 371 (c)(1),
(2), (4) Date: Jul. 23, 2010

(87) PCT Pub. No.: WO2009/092710
PCT Pub. Date: Jul. 30, 2009

(65) Prior Publication Data
US 2011/0002760 A1 Jan. 6, 2011

(30) Foreign Application Priority Data
Jan. 24, 2008 (IT) .............................. MI2008A0101

(51) Int. Cl.
*B65G 47/24* (2006.01)
(52) U.S. Cl.
USPC ....... 198/397.06; 198/890; 221/165; 209/653
(58) Field of Classification Search
USPC .............. 198/397.06, 890; 221/165; 209/652, 209/653
See application file for complete search history.

(56) References Cited

U.S. PATENT DOCUMENTS

| | | | | |
|---|---|---|---|---|
| 2,026,172 A * | 12/1935 | Holm | ........................ | 198/468.2 |
| 2,252,498 A * | 8/1941 | Flaws, Jr. | ........................ | 221/14 |
| 2,790,532 A * | 4/1957 | Albertoli | ........................ | 198/389 |
| 3,148,762 A * | 9/1964 | Gleason | ........................ | 198/389 |
| 3,517,797 A * | 6/1970 | Rappo et al. | ........................ | 198/389 |
| 3,823,815 A * | 7/1974 | Bretten et al. | ........................ | 198/389 |
| 4,099,609 A * | 7/1978 | Kieronski et al. | ........................ | 198/395 |
| 4,223,778 A * | 9/1980 | Kontz | ........................ | 198/389 |
| 4,244,459 A * | 1/1981 | Garrett | ........................ | 198/389 |

(Continued)

FOREIGN PATENT DOCUMENTS

| | | |
|---|---|---|
| DE | 88 02 825 U1 | 4/1988 |
| EP | 0 452 857 A1 | 10/1991 |
| JP | 2000-19182 A | 1/2000 |
| JP | 2000-168945 A | 6/2000 |

*Primary Examiner* — Joseph Dillon, Jr.
(74) *Attorney, Agent, or Firm* — Birch, Stewart, Kolasch & Birch, LLP

(57) ABSTRACT

There is described an apparatus for loading test tubes (1) in conveying devices (6) included in an automatic conveyor (7) for test tubes, comprising a recruiting device (2) for test tubes adapted to feed test tubes to a positioning device (4) for test tubes having a lane (15, 16) consisting of two spaced, parallel walls (17) on the edges of which respective motorized belts (18) slide, the distance between said walls (17) forming the lane (15) being adjustable and such that a test tube makes a 90° rotation when horizontally falling from the recruiting device (2), thus remaining vertically hanging and resting on the belts (18) by the projecting part of the cap with respect to the lateral body of the test tube. The belts (18) convey the test tube to a loading area (8) where the test tubes are handled by a test tube handling device (5) to a working point (9) included in the conveyor (7) adapted to automatically convey test tubes from and to modules for preparing and analyzing biological material.

6 Claims, 7 Drawing Sheets

(56) References Cited

U.S. PATENT DOCUMENTS

| | | | | |
|---|---|---|---|---|
| 4,550,820 A | * | 11/1985 | Bishop | 198/389 |
| 4,610,345 A | * | 9/1986 | Spreen et al. | 198/392 |
| 4,696,144 A | * | 9/1987 | Bankuty et al. | 53/331.5 |
| 4,819,785 A | * | 4/1989 | Ichizawa et al. | 198/404 |
| 4,938,649 A | * | 7/1990 | ter Horst et al. | 414/412 |
| 5,174,430 A | * | 12/1992 | Ebira | 198/418.5 |
| 5,314,055 A | * | 5/1994 | Gordon | 198/395 |
| 5,333,718 A | * | 8/1994 | Pannell et al. | 198/397.06 |
| 5,439,093 A | * | 8/1995 | Drewitz | 198/399 |
| 6,341,630 B2 | * | 1/2002 | Reinecke | 141/168 |
| 6,374,986 B1 | * | 4/2002 | Oe | 198/396 |
| 6,430,896 B1 | * | 8/2002 | Torikian | 53/310 |
| 6,581,355 B1 | * | 6/2003 | Yuyama et al. | 53/135.1 |
| 7,322,458 B1 | * | 1/2008 | McDonald et al. | 198/389 |
| 7,556,137 B2 | * | 7/2009 | Charpentier | 198/395 |
| 8,074,781 B1 | * | 12/2011 | Reardon, Jr. | 198/392 |
| 8,151,970 B2 | * | 4/2012 | McDonald et al. | 198/389 |
| 8,397,473 B2 | * | 3/2013 | Pedrazzini | 53/317 |
| 8,413,789 B2 | * | 4/2013 | Cassoni et al. | 198/397.01 |
| 8,463,427 B2 | * | 6/2013 | Pedrazzini | 700/230 |
| 2004/0084282 A1 | * | 5/2004 | Hellmann et al. | 198/540 |
| 2004/0144618 A1 | | 7/2004 | McDonald et al. | |
| 2006/0070848 A1 | * | 4/2006 | Saito | 198/396 |
| 2007/0158163 A1 | * | 7/2007 | Kritzinger et al. | 198/397.06 |
| 2010/0012460 A1 | * | 1/2010 | Pedrazzini | 198/394 |
| 2010/0034701 A1 | * | 2/2010 | Pedrazzini | 422/65 |
| 2010/0233754 A1 | * | 9/2010 | Guex | 435/29 |
| 2010/0307109 A1 | * | 12/2010 | Pedrazzini | 53/317 |
| 2010/0312379 A1 | * | 12/2010 | Pedrazzini | 700/230 |
| 2011/0045958 A1 | * | 2/2011 | Pedrazzini | 494/8 |
| 2011/0112683 A1 | * | 5/2011 | Pedrazzini | 700/218 |
| 2011/0158850 A1 | * | 6/2011 | Pedrazzini | 422/65 |
| 2012/0055756 A1 | * | 3/2012 | Reardon, Jr. | 198/380 |
| 2012/0058010 A1 | * | 3/2012 | Pedrazzini | 422/63 |
| 2013/0058752 A1 | * | 3/2013 | Pedrazzini | 414/751.1 |

* cited by examiner

APPARATUS FOR LOADING BIOLOGICAL MATERIAL CONTAINERS IN A CONVEYING SYSTEM

The present invention relates to an apparatus for loading biological material containers in a conveying system.

The Laboratory Medicine progress noticed during the last twenty years led analysis laboratories to promote the use of machines directed to automate the laboratory tests, thus obtaining several advantages such as an acceleration of tests and a greater safety for the laboratory operators who are less and less involved in directly handling potentially infected biological materials to be analysed, since they simply have to manage the machines.

The construction of an automated working chain which is able to comprise the various steps of processing the biological material (preparation, real analysis and possible preservation) is an increasingly common desire in all average-large sized analysis laboratories, where large work loads are found every day.

By automated working chain it is intended a set of devices serving the function of processing the biological materials, included in a conveyor belt adapted to exhibit the biological material containers to said devices, thus managing the processing thereof and storing their life cycle.

There is a clear need for ensuring an equal efficiency in each single step of the working chain, in order to avoid "bottlenecks" which could cause a slowing down when processing the biological material specimens, therefore limiting the great advantages provided by the introduction of automation.

A possible slowing down could be represented by the step of inserting the containers into the automation, which action necessarily requires a high dexterity by the laboratory operator.

It is the object of the present invention to provide the analysis laboratories with devices serving the function of loading the biological material containers in the automatic conveying systems, in order to avoid human intervention as much as possible, thus limiting times and ensuring the laboratory operators safety, as desired.

In accordance with the invention, the object is achieved by an apparatus for loading test tubes in conveying devices included in an automatic conveyor for test tubes, characterized in that it comprises a device for recruiting test tubes adapted to feed the test tubes to a device for positioning the test tubes having a lane consisting of two spaced, parallel walls on the edges of which respective motorized belts slide, the distance between said lane-forming walls being adjustable and such that a test tube makes a 90° rotation when horizontally falling from the recruiting device, thus remaining vertically hanging and resting on the belts by the projecting part of the cap with respect to the lateral body of the test tube, the belts conveying the test tube to a loading area where the test tubes are handled by a device for handling test tubes to a working point included in the conveyor adapted to automatically convey test tubes from and to modules for preparing and analyzing the biological material.

The device for positioning test tubes plays the role of ensuring a correct position of the test tubes recruited by the recruiting device: in order to be then loaded in a suitable conveying device on the conveyor, the test tube is to be exhibited to the handling device in a position such that the whole processing required by the interfaced modules on the conveyor may be carried out thereon. The required position is the vertical one, with the cap facing upwards. The test tubes contained in the hopper are further believed to be all sealed in order to avoid biological material dispersions.

Therefore, the described apparatus is included in a context of overall automation of the whole working cycle carried out on the biological material specimens in an analysis laboratory.

These and other features of the present invention will be made more apparent from the following detailed description of a practical embodiment thereof, shown by way of non limitative example in the accompanying drawings, in which:

FIG. 1 shows a perspective view of the apparatus adapted to load test tubes in conveying devices included in a conveyor;

FIG. 2 shows a top view of the configuration in FIG. 1;

FIG. 3 shows a perspective view of the recruiting device;

FIG. 4 shows a side view of the configuration in FIG. 3;

FIG. 5 shows a perspective view of the positioning device;

FIG. 6 shows a section view according to line VI-VI of the configuration in FIG. 2 (only the section related to the positioning device has been depicted for the sake of clarity);

FIG. 7 shows a bottom perspective view of the configuration in FIG. 5.

FIG. 1 shows an apparatus adapted to load test tubes 1, comprising a recruiting device 2 playing the role of recruiting test tubes 1 from a hopper 3 and exhibiting said test tubes to a positioning device 4.

Said positioning device 4 has the task of positioning test tubes 1 by arranging them in a vertical position with the cap facing upwards, so that they may be gripped by a handling device 5 for test tubes 1 and arranged in conveying devices 6 included in a conveyor 7 (FIG. 1) adapted to automatically convey test tubes 1 to and from processing modules, as described in the Italian Patent Application No. MI2007A002254.

In detail, the handling device 5 handles test tubes 1 from a loading area 8 included in the positioning device 4 to an unloading area 9 included in the conveyor 7, as depicted in FIG. 2 (the handling device 5 has been depicted by a dashed rectangle for a better view of the loading/unloading areas).

The recruiting device 2 (FIGS. 3 and 4) consists of fixed combs 11 and movable combs 12. As indicated by the arrows in FIG. 4, the movable combs 12 move on the fixed combs 11 thus recruiting the test tubes 1 from the hopper 3 and moving them upwards, on the following uppermost fixed combs.

Coinciding with the uppermost fixed comb 13, at the top of the system of fixed combs 11 there is a chute 14 on which a test tube 1 recruited from the hopper 3, in the position shown in FIG. 3, slides to arrange itself on the positioning device 4 (FIGS. 2 and 3).

The positioning device 4 (FIG. 5) comprises a pair of lanes adapted to position test tubes having different dimensions: a lane 15 and a lane 16 of different widths. In this particular case, as almost all the test tubes containing biological material, such as blood, which are marketed and used in the analysis laboratories are differentiated into test tubes having a 13 mm diameter and test tubes having a 16 mm diameter, the disclosed embodiment presents a lane 15 adapted to position test tubes having a 13 mm diameter and a lane 16 adapted to position test tubes having a 16 mm diameter. However, it should be specified that the described device may be adapted to position test tubes of any diameter, by simply dimensioning the lanes in a suitable manner.

The described positioning device is based on the assumption that the cap applied to a test tube and adapted to ensure the sealing thereof, projects by some millimeters from the lateral body of the test tube.

Figure 6:
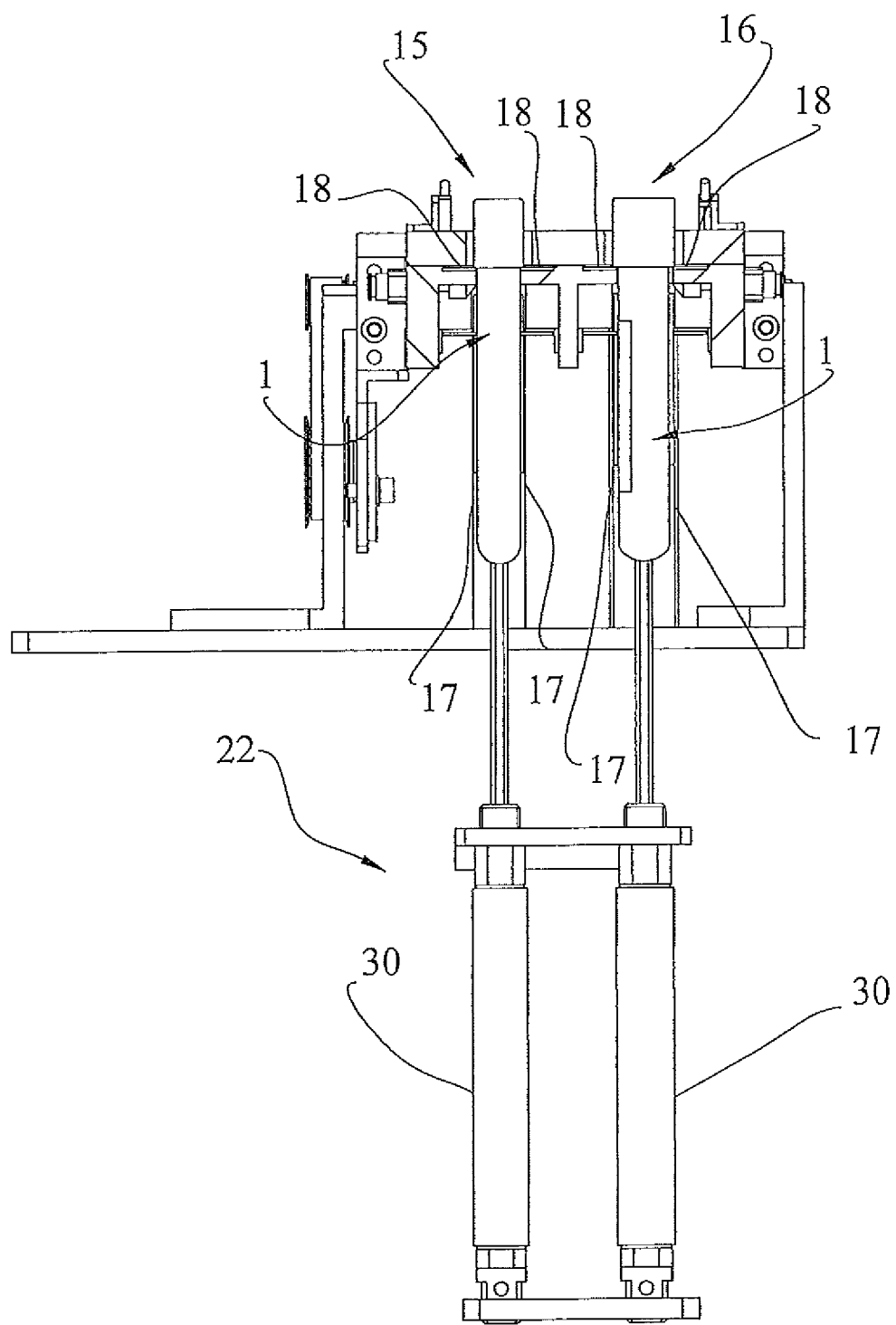
Figure 7:
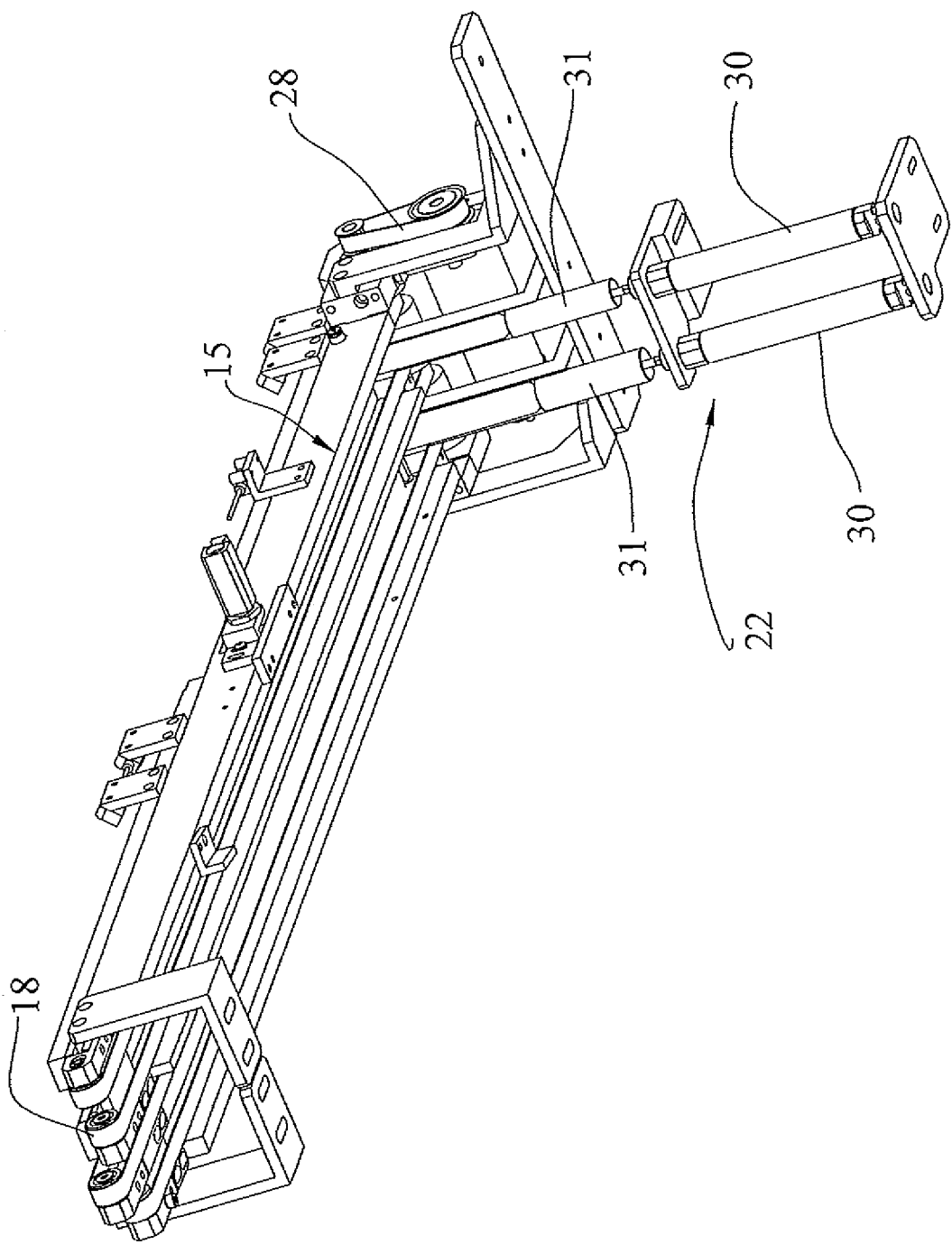

Each lane consists of two walls 17 which are spaced and parallel to each other and adapted to form a path, furthermore belts 18 (FIGS. 6 and 7) slide on the edge of each wall 17.

Figure 5:
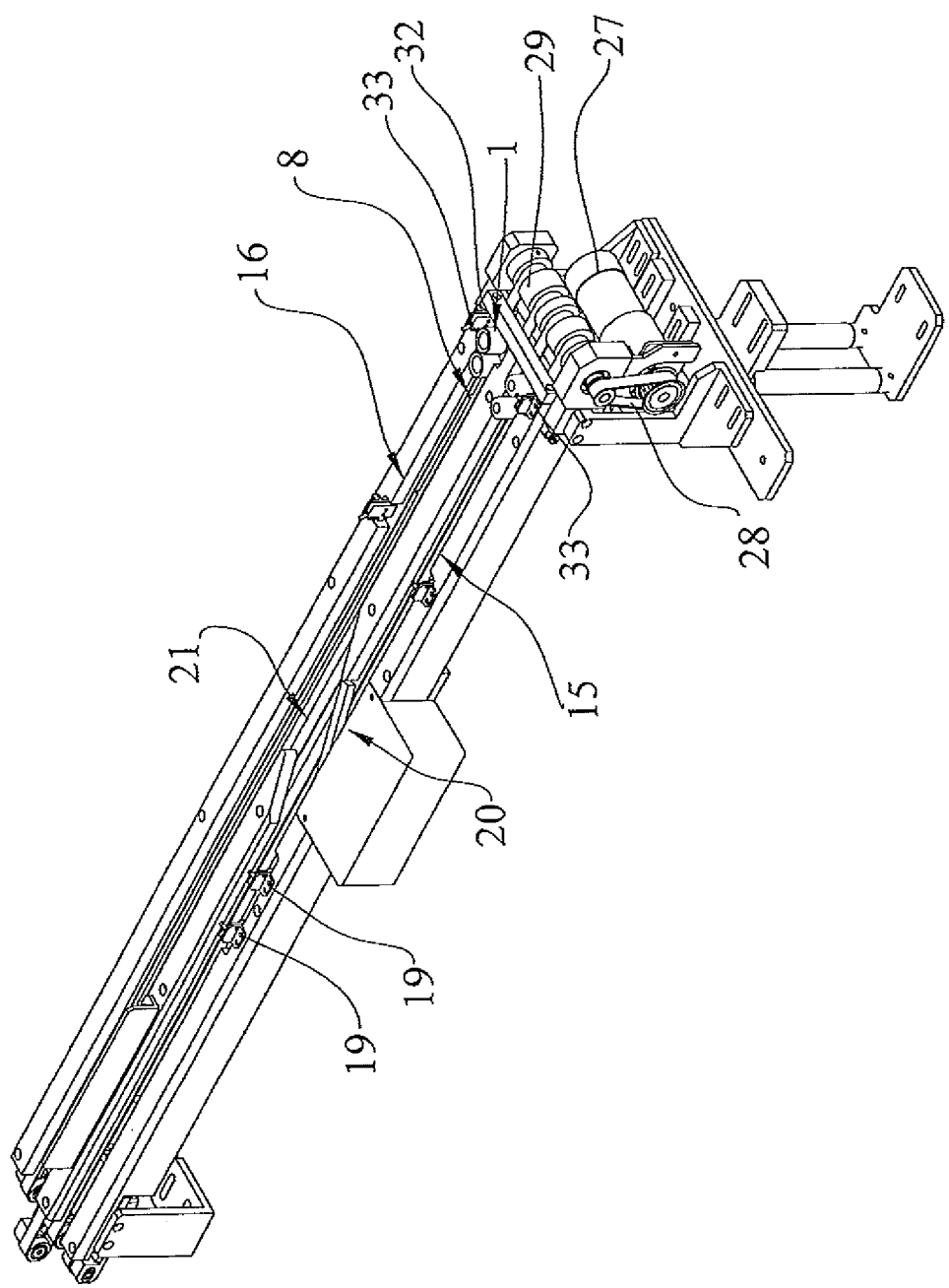

The distance between the walls 17 forming the lane 15 is such that a test tube having a 13 mm diameter, when falling in laying down position from the chute 14, performs a 90° rotation by remaining hanging and resting on the belts by means of the projecting part of the cap with respect to the lateral body. While sliding, the belts 18 convey the test tube to the loading area 8 (FIG. 5).

When falling from the chute 14 to the lane 15, test tubes having a 16 mm diameter lay down as they are wider than said lane which is adapted to position the test tubes having a 13 mm diameter only.

The positioning device 4 is equipped with recognizing devices 19 (FIG. 5) which are adapted to discriminate laying down test tubes against straightened test tubes and convey the former having a larger diameter on the lane 16 adapted to position test tubes of different dimensions.

In the described embodiment, the recognizing device 19 consists of two presence sensors placed on the lane 15, which activate a diverter 20 close to a diversion 21 when intercepting the laying down test tube. Said diverter 20 prevents the test tube from following the path on the lane 15 by diverting the laying down test tube to the lane 16 of a larger width, where the same positioning process occurs as previously described.

The belts 18 convey the so straightened test tube to the loading area 8.

Said loading area 8 consists of two working points, one on each lane 15-16 (FIG. 5).

Therefore, the test tubes divided on the two lanes reach the loading area 8 where they queue up awaiting for being loaded by the handling device 5 and unloaded on the conveyor 7.

There is a lifting device 22 inside the loading area 8 (FIG. 7), which plays the role of lifting the test tubes to be loaded such that the bottom of the test tube is always positioned at the same altitude, regardless of the height of the test tube itself.

For a better comprehension, we specify that the test tubes currently marketed and used in the analysis laboratories may also be of different heights, as well as have different diameters, according to the amount of biological material to be contained and to the type of analysis to be carried out thereon.

The reason why the test tubes are desired to be positioned at the same altitude during the step of loading, apart from their heights, is to allow the handling device 5 to be able to always position them at the same altitude on the conveyor 7, in the specific conveying devices 6.

This results from the fact that the handling device 5 is formed by a pneumatically operated mechanical arm capable of gripping the test tubes and releasing them, as it is able to reach all the points needed to accomplish the required operations, but capable of always reaching the same altitude only during the vertical movements.

Figure 1:
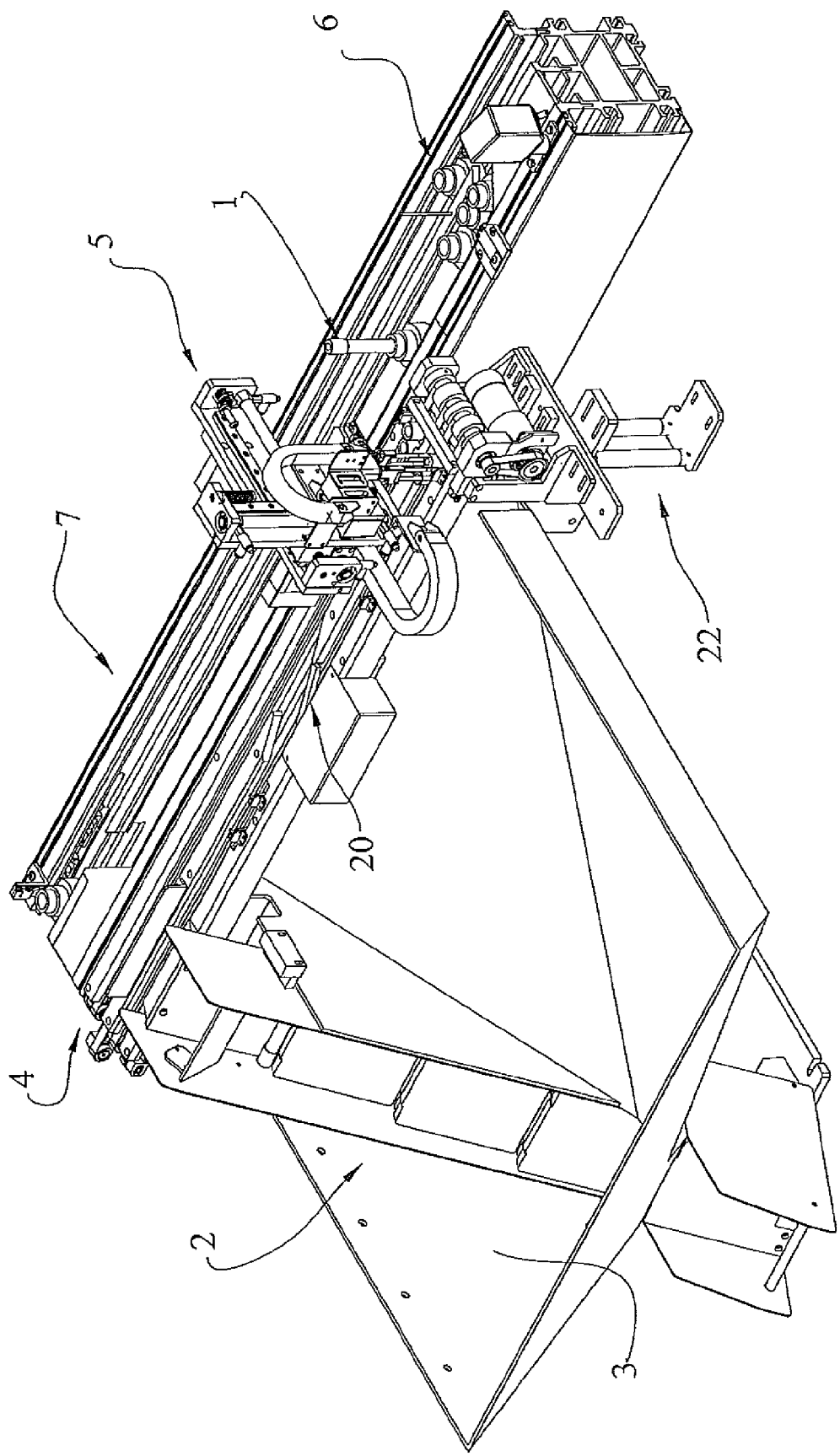
Figure 2:
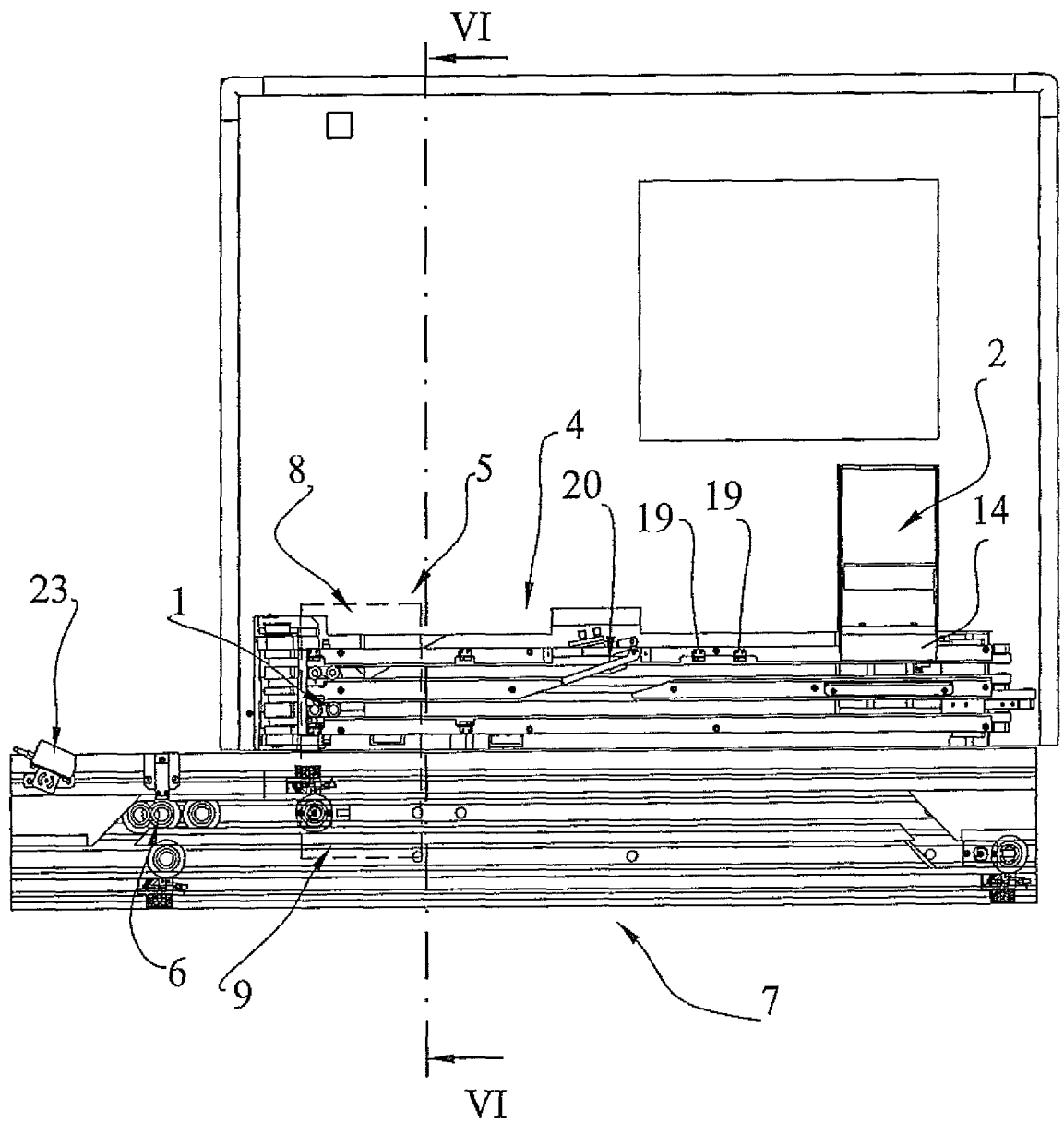

The test tubes loaded in the conveying devices 6, possibly identified by suitable recognizing devices 23 (FIG. 2), are conveyed by the conveyor belt towards further processing or analysis modules which are interfaced with the conveyor 7.

Figure 3:
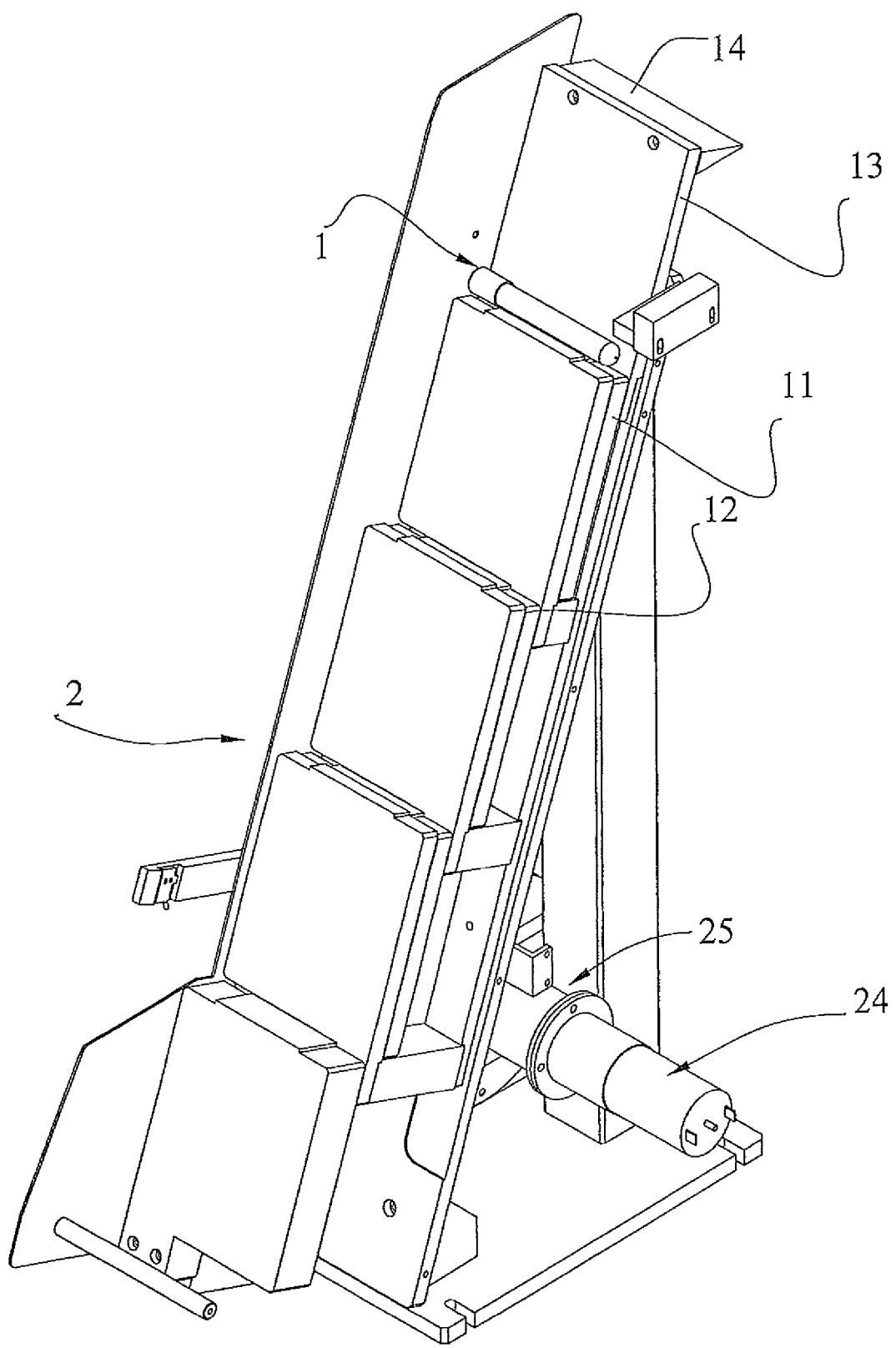
Figure 4:
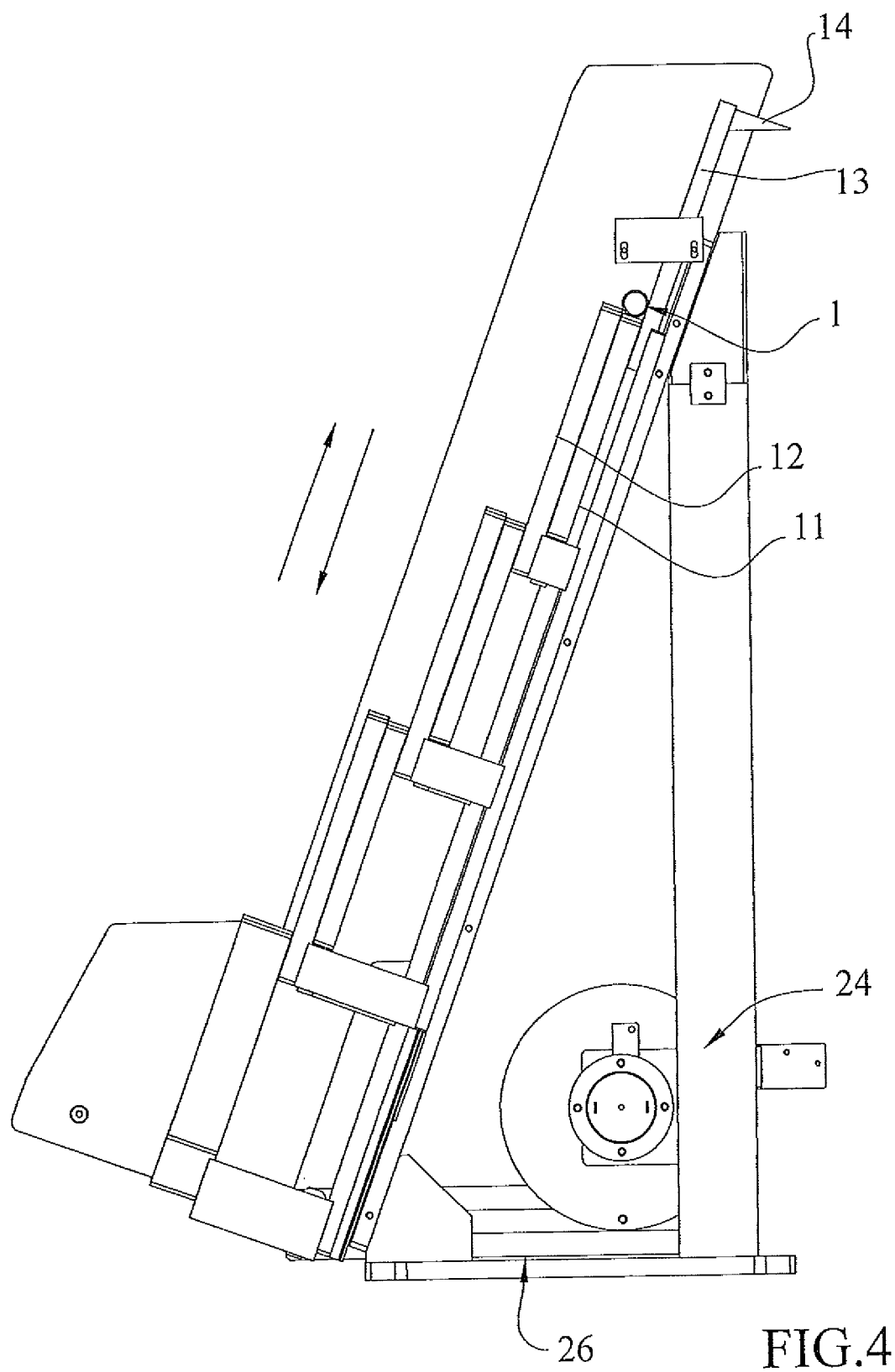

The system of movable combs 12 included in the recruiting device 2 is actuated by an electric motor 24 which actuates a movable arm 26 by means of a transmission 25 thus generating the stroke of the movable combs on the fixed ones (FIGS. 3 and 4).

The belts 18 of the positioning device 4 are actuated by an electric motor 27, the rotational movement of which is transmitted through a drive belt 27 to a shaft 29 on which the belts slide (FIG. 5).

The lifting device 22 (FIG. 7) consists of two cylinders 30 adapted to lift two sockets 31 placed underneath the stopping points of the test tube, in the two loading points on the lanes 15 and 16.

The stopping point is determined by the profile 32 (FIG. 5) which determines the stop of the lanes 15 and 16, Presence sensors 33 placed on the lanes control the actual presence of the test tube to be loaded; such information is sent to the handling device 5 for starting the loading/unloading process.

The invention claimed is:

1. An apparatus for loading test tubes in conveying devices included in an automatic conveyor for test tubes, comprising:
   a hopper;
   a positioning device for test tubes having a first lane and a second lane, each lane comprising two spaced, parallel walls forming an opening between the walls, and motorized belts sliding on edges of the walls, the belts located above a top edge of the walls; and
   a recruiting device having an elevated end, the recruiting device providing test tubes to the positioning device in a horizontal orientation, each test tube having a cap extending laterally from a sidewall of the test tube;
   wherein a distance between said walls forming the first lane is such that a test tube having a first diameter rotates from the horizontal orientation from the recruiting device to a vertical orientation,
   wherein the cap engages the belts at the edges of the walls, the belts conveying the test tube to a loading area where the test tubes are handled by a test tube handling device to a working point included in the conveyor, the conveyor adapted to automatically convey the test tubes from and to modules for preparing and analyzing biological material, and
   wherein the positioning device further comprises:
      sensors on the first lane, which are adapted to discriminate between horizontally oriented test tubes and vertically oriented test tubes; and
      diverters adapted to move the horizontally oriented test tubes to the second lane, the second land having a larger width than the first lane, the test tubes moved to the second lane adopting a vertical orientation in the second lane.

2. An apparatus according to claim 1, wherein the loading area comprises a lifting device adapted to lift the test tubes to be loaded, so that the bottom of the test tube is always positioned at the same altitude, regardless of the height of the test tube itself, to allow the test tubes to be always loaded in the conveying devices at the same altitude.

3. An apparatus according to claim 1, wherein said positioning device further comprises an electric motor which controls the rotation of a shaft on which the belts slide by means of a drive belt.

4. An apparatus according to claim 2, wherein said positioning device further comprises an electric motor which controls the rotation of a shaft on which the belts slide by means of a drive belt.

5. An apparatus according to claim 1, wherein the distance between the walls of the first lane is adjustable.

6. An apparatus according to claim 1, wherein the belts have a horizontal abutment surface laying upon the opening.

* * * * *